United States Patent
Rao et al.

(10) Patent No.: US 6,699,717 B1
(45) Date of Patent: *Mar. 2, 2004

(54) METHOD USING LUMINESCENT TRANSITION METAL-LIGAND COMPLEX FOR DETECTING POLAR SOLVENTS

(75) Inventors: Govind Rao, Columbia, MD (US); Qing Chang, Carmel, IN (US); Joseph R. Lakowicz, Ellicott City, MD (US); Zakir Murtaza, Vernon Hills, IL (US)

(73) Assignees: The University of Maryland Baltimore County, Baltimore, MD (US); The University of Maryland Biotechnology Institute, Baltimore, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/799,410

(22) Filed: Feb. 12, 1997

(51) Int. Cl.[7] .............................................. G01N 21/64
(52) U.S. Cl. ......................... 436/39; 436/132; 436/172
(58) Field of Search ...................... 422/82.08; 436/164, 436/166, 172, 39, 40, 131, 132; 250/459.1

(56) References Cited

U.S. PATENT DOCUMENTS

| | | | |
|---|---|---|---|
| 2,420,286 A | | 5/1947 | Lacey et al. |
| 4,495,293 A | | 1/1985 | Shaffar |
| 4,656,141 A | | 4/1987 | Birks et al. |
| 4,743,561 A | | 5/1988 | Shaffar |
| 5,094,819 A | | 3/1992 | Yager et al. |
| 5,118,405 A | * | 6/1992 | Kaneko et al. .............. 204/433 |
| 5,221,605 A | * | 6/1993 | Bard et al. ....................... 435/4 |
| 5,374,562 A | | 12/1994 | Simon |
| 5,468,644 A | | 11/1995 | Stephenson et al. |
| 5,470,755 A | | 11/1995 | Simon |
| 5,485,530 A | | 1/1996 | Lakowicz et al. |
| 5,580,527 A | * | 12/1996 | Bell et al. ................. 422/82.07 |
| 5,585,279 A | * | 12/1996 | Davidson ..................... 436/546 |

FOREIGN PATENT DOCUMENTS

WO    WO 96/13722    10/1995

OTHER PUBLICATIONS

McMurray, H. Neil, et al., "Oxygen quenching of tris (2,2'–bipyridine) ruthenium (II) complexes in thing organic films," J. Photochem. Photobiol. A., vol. 80, No. 1–3, 1994, pp. 283–288.

Toliolo, Rosanna, et al., "Amperometric Determination of Peroxides by Glassy Carbon Electrodes Modified with Copper–Phenanthroline Complexes," Electroanalysis, vol. 8, No. 2, 1996, pp. 151–157.

Szmacinski, Henry et al., "Optical Measurements of pH Using Fluorescence Lifetimes and Phase–Modulation Fluorometry," Analytical Chemistry, 65, (1993), 1668–1674.

Demas, J. N. et al., "Design and Applications of Highly Luminescent Transition Metal Complexes," Analytical Chemistry, 63:17, (1991) 829A–837A.

Sipior, Jeffrey et al., "Phase Fluorometric Optical Carbon Dioxide Gas Sensor for Fermentation Off–Gas Monitoring," Biotechnol. Prog., 12, (1996), 266–271.

Kumoi, Sadakatsu et al., "Spectrophotometric Determination of Water in Organic Solvents With Solvatochromic Dyes–II*," Talanta, 19, (1972), 505–513.

Reichardt, Christian et al., "Solute/solvent interactions and their empirical determination by means of solvatochromic dyes," Pure & Appl. Chem., 65:12, (1993), 2593–2601.

Brooker, Leslie G.S. et al., "Color and Constitution. XIII. Merocyanines as Solvent Property Indicators," J. Amer. Chem. Soc., 87,(1965), 2443–2450.

Gordon, John E., "Transition Energies for a Merocyanine Dye in Aqueous Electrolyte Solutions. Solvent Polarity Indicator Transition Energy–Internal Pressure Relations," The Journal of Physical Chemistry, 70:7, (1966), 2413–2416.

Figueras, J., "Hydrogen Bonding, Solvent Polarity, and the Visible Spectrum of Phenol Blue and Its Derivatives," J. Amer. Chem. Soc., 93, (1971), 3255–3263.

Kolling, Orland W. et al., "Phenol Blue as a Solvent Polarity Indicator for Binary Aprotic Solvents," Analytical Chemistry, 45:1, (1973), 160–164.

Kolling, Orland W. , "Spectrophotometric Measurement of Solvent Polarity with Phenol Blue as the Probe," Anal. Chem., 53, (1981), 54–56.

Terpetschnig, Ewald, "Metal–Ligand Complexes as a New Class of Long–Lived Fluorophores for Protein Hydrodynamics," Biophysical Journal, 68, (1995), 342–350.

Hubert, Christine et al., "Polymer Communications," Polymer, 36:13, (1995), 2663–2666.

Chang, Qing et al., "A Lifetime–Based Fluorescence Resonance Energy Transfer Sensor for Ammonia," Analytical Biochemistry, 232, (1995), 92–97.

Sipior, Jeffrey et al., "A Lifetime–Based Optical $CO_2$ Gas Sensor with Blue or Red Excitation and Stokes or Anti-Stokes Detection," Analytical Biochemistry, 227, (1995), 309–318.

Reichardt, Christian, "Solvatochromic Dyes as Solvent Polarity Indicators," Chem. Rev., 94, (1994), 2319–2358.

Kumoi, Sadakatsu et al., "Spectrophotometric Determination of Water in Organic Solvents With Solvatochromic Dyes*," Talanta, 19, (1970), 319–327.

* cited by examiner

Primary Examiner—Jeffrey Snay
(74) Attorney, Agent, or Firm—Gary M. Nath; Todd L. Juneau

(57) ABSTRACT

The present invention relates to a transition metal-ligand complex that shows changes in its luminescence lifetime characteristic and/or luminescence intensity as a function of the polarity and/or hydrogen bonding properties of its environment, and a sensor, probe, system and method based on the complex for detecting the presence, amount or concentration of a polar solvent in a medium.

23 Claims, 14 Drawing Sheets

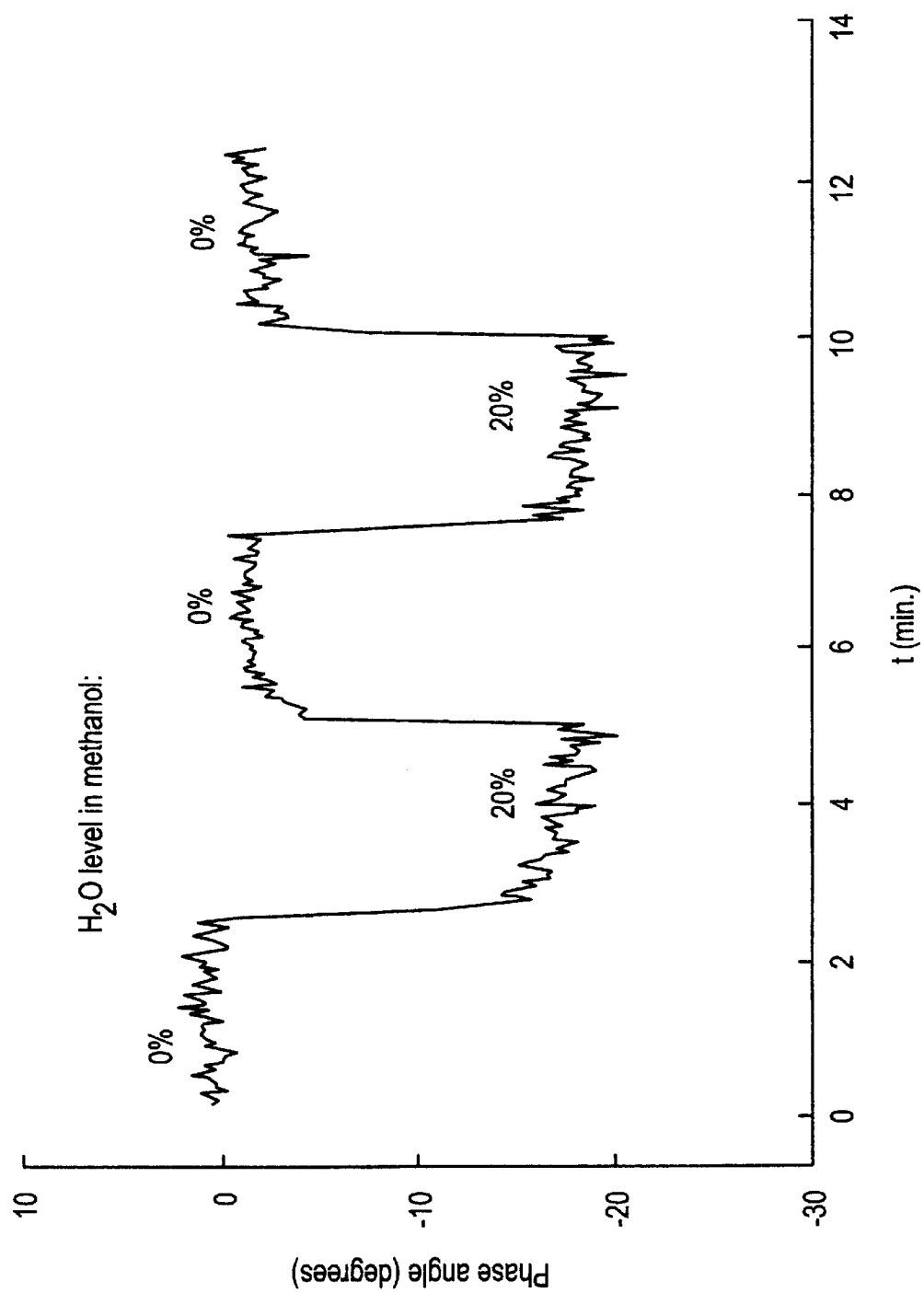

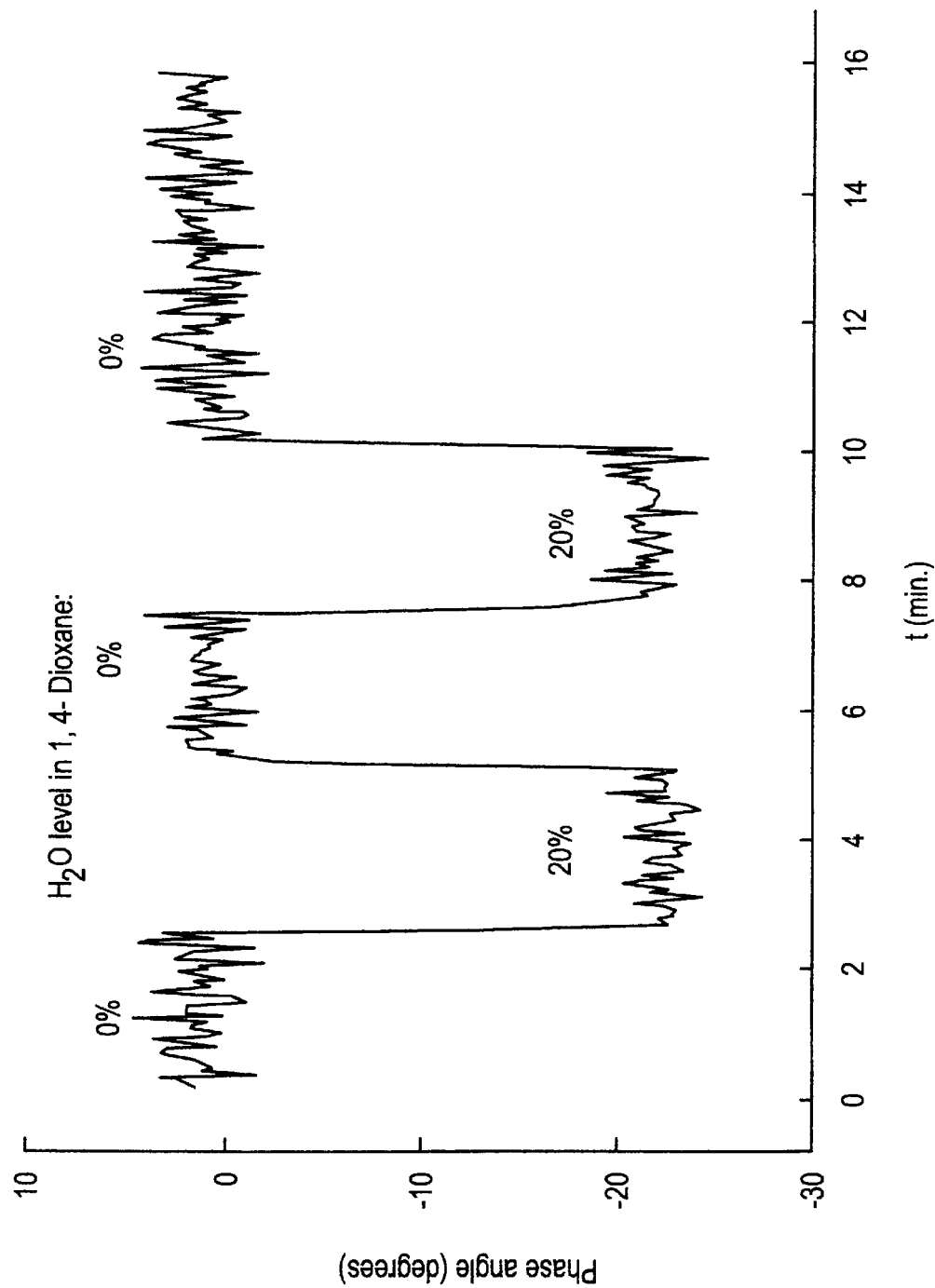

METHOD USING LUMINESCENT TRANSITION METAL-LIGAND COMPLEX FOR DETECTING POLAR SOLVENTS

BACKGROUND OF THE INVENTION

1. Field of Invention

The present invention relates to a transition metal-ligand complex that shows changes in its luminescence lifetime characteristic and/or luminescence intensity as a function of the polarity and/or hydrogen bonding properties of its environment, and a sensor, probe, system and method based on the complex for detecting the presence, amount or concentration of a polar solvent in a medium.

2. Description of Related Art

There is extensive interest in optical chemical sensing in the fields of bio-engineering, environmental science and industry. Fiber Optic Chemical Sensors and Biosensors, ed. Wolfbeis, O. S., CRC Press, Boca Raton, Fla., 1991, vols. I and II; Topics in Fluorescence Spectroscopy. Volume 4: Probe Design and Chemical Sensing, ed. Lakowicz, J. R., Plenum Press, New York, 1994; Seitz, W. R., CRC Crit. Rev. Anal. Chem., 1988, 19, 135; Rao, G., Bambot, S. B., Kwong, C. W., Szmacinski, H., Sipior, J., Holavanahali, R., and Carter, G., in Topics in Fluorescence Spectroscopy. Volume 4: Probe Design and Chemical Sensing, ed. Lakowicz, J. R., Plenum Press, New York, 1994, pp. 417–448. Among a number of sensing schemes, luminescence lifetime-based sensing is one of the preferred methods, because of its unique advantages of being insensitive to signal drift resulting from leaching and photobleaching of indicator dye, variations of light source intensity, and stability of the photodetector.

Although sensors based on the principle of phase-modulation fluorometry have been reported for sensing pH (Szmacinski, H. S., and Lakowicz, J. R., Anal. Chem., 1993, 65, 1668), $CO_2$ (Sipior, J., Bambot, S., M., Romauld, Carter, G. M., Lakowicz, J. R., and Rao, G., Anal. Biochem., 1995, 227, 309), $NH_3$ (Chang, Q., Sipior, J., Lakowicz, J. R., and Rao, G., Anal. Biochem., 1995, 232, 92) and glucose (Lakowicz, J. R, and Maliwal, B. P., Anal. Chim. Acta, 1993, 271, 155), none has heretofore been developed for sensing polar solvents, such as methanol, ethanol and water.

A methanol or ethanol sensor is of great interest for various applications, particularly in the chemical and biochemical processing industries. For example, such a sensor would be useful in the petroleum industry for measuring and controlling the concentration of methanol and ethanol, which have replaced tetraethyl lead as the anti-knocking agent in most gasoline products. In the biochemical engineering industry, methanol and ethanol bio-sensors have been used to monitor and control methanol concentration in polysaccharide fermentation (Austin, G. D., Sankhe, S. K., and Tsao, G. T., Bioprocess Eng., 1992, 7, 241), and ethanol concentration in yeast fermentation (Paul, C. D., and Maerz, U., Biotechnol. Educ., 1991, 2, 59). Additionally, a methanol sensor would be useful in chromatographic and other separations where methanol is widely used.

Because methanol is a very polar molecule, a sensor for detecting methanol in non-polar media can be constructed using a solvatochromic indicator dye. Although solvatochromic dyes have been used for decades as polarity indicators in solutions (Reichardt, C., Solvent and Solvent Effects in Organic Chemistry, VCH Publishers, New York, 2nd edn., 1988; Reichardt, C., Chem. Rev., 1994, 94, 2319; Kumoi, S., Oyama, K., Yano, T., Kobayashi, H., and Ueno, K., Talanta, 1970, 17, 319; Kumoi, S., Kobayashi, H., and Ueno, K., Talanta, 1972, 19, 505; Reichardt, C., Asharin-Fard, S., Blum, A., Eschner, M., Mehranpour, A. M., Milart, P., Niem, T., Schafer, G., and Wilk, M., Pure and Appl. Chem., 1993, 65, 2593; Kolling, O. W., Anal. Chem., 1981, 53, 54; Kolling, O. W., and Goodnight, J. L., Anal. Chem., 1973, 45, 160; Figueras, J., J. Am. Chem. Soc., 1971, 93, 3255; Gaines, G. L., Jr., Anal. Chem., 1976, 48, 450; Gordon, J. E., J. Phys. Chem., 1966, 70, 2413; and Brooker, L. G. S., Craig, A. C., Heseltine, D. W., Jenkins, P. W., and Lincoln, L. L., J. Am. Chem. Soc., 1965, 87, 2443), they did not become a part of any practically useful methanol sensor until Hubert and coworkers reported using them in a polymer film sensor for detecting polar additives in hydrocarbon blends. Hubert, C., Fichou, D., Valat, P., Garnier, F., and Villeret, B., Polymer, 1995, 36, 2663. Specifically, Hubert et al. created a polymer film for sensing small polar molecules, such as methanol and ethanol, by doping Reichardt's dye in a poly(methyl methacrylate) (PMMA) polymer matrix, and spin-coating the mixture on a piece of glass slide. The film displayed an absorption maximum at 654 nm in methanol-free naphtha, which moved to 542 nm in a mixture of 2% methanol in naphtha. By monitoring the absorbance change at 654 nm, the sensor could detect methanol at a level down to 0.1% concentration. A drawback to Hubert et al.'s sensor is that it requires careful pre-treatment before measuring because it is subject to interference from atmospheric humidity. Additionally, the present inventors have found in a preliminary experiment that Reichardt's dye is not photostable. Such instability will limit the use of the sensor in practice.

Besides methanol and ethanol, another solvent that can be detected by a polar sensor is water. Water is the most common impurity or contaminant in many organic solvents, particularly solvents that are miscible with water. As such, a sensor capable of detecting the presence and amount of water would be useful in numerous applications, including, for instance, detecting gasoline leakage from tanks, measuring the organic (or water) content in waste industrial liquid, and monitoring the alcohol content in processes for fermenting liquor. As discussed later in this application, such a water sensor can be constructed based on the principle of luminescence lifetime, using a transition metal-ligand complex as an indicating molecule immobilized in a hybrid solid support of organic polymer, carboxymethyl cellulose, and inorganic polymer (sol-gel). An advantage of using luminescent metal-ligand complexes is their long decay times over 100 ns, which allow simple and low cost instrumentation for lifetime based sensing.

Based on the foregoing background, a need exists for a new and improved sensor to detect the presence, amount and/or concentration of polar solvents, such as methanol, ethanol and water.

SUMMARY OF THE INVENTION

The inventors have discovered a novel transition metal-ligand complex that is useful as a sensor for detecting and measuring a physical and/or chemical characteristic of a sample, such as monovalent or divalent cation concentration, anion concentration, oxygen concentration, pH, viscosity and polarity.

Specifically, their invention relates to a transition metal-ligand complex, which comprises:

(i) a transition metal; and (ii) at least one bi- or tri-dentate imine ligand.

In a preferred embodiment, the complex has a luminescence lifetime characteristic that changes as a function of the polarity or hydrogen bonding properties of its environment.

In another preferred embodiment, the intensity of luminescence emitted by the complex changes as a function of the polarity or hydrogen bonding properties of its environment.

The invention further relates to a sensor for use in determining the presence, amount or concentration of a polar solvent in a medium, which comprises a transition metal-ligand complex containing a transition metal and at least one bi- or tri-dentate imine ligand.

Additionally, the invention relates to a method for determining the presence, amount or concentration of a polar solvent in a medium, which comprises:

(ii) determining, in the absence of the polar solvent, a luminescence lifetime characteristic of a sensor, wherein the sensor comprises a transition metal-ligand complex containing a transition metal and at least one bi- or tri-dentate imine ligand;

(iii) contacting the medium with said sensor;

(iii) determining a change in the luminescence lifetime characteristic of said sensor; and (iv) determining the presence, amount or concentration of the polar solvent in the medium based on the change in the luminescence lifetime characteristic of said sensor.

The invention also relates to a method for determining the presence, amount or concentration of a polar solvent in a medium, which comprises:

(i) determining, in the absence of the polar solvent, the intensity of luminescence emitted by a sensor, wherein the sensor comprises a transition metal-ligand complex containing a transition metal and at least one bi- or tri-dentate imine ligand;

(iii) contacting the medium with said sensor;

(iii) determining a change in the luminescence intensity of said sensor; and (iv) determining the presence, amount or concentration of the polar solvent in the medium based on the change in the luminescence intensity of said sensor.

Furthermore, the invention relates to a probe for determining the presence, amount or concentration of a polar solvent in a medium, which comprises:

(i) a sensor comprising a transition metal-ligand complex containing a transition metal and at least one bi- or tri-dentate imine ligand; and (ii) connected to the sensor, optical transmission means for transmitting luminescence excitation radiation to the sensor and transmitting luminescence emitted by the sensor to a detector.

Finally, the invention relates to a system for determining the presence, amount or concentration of a polar solvent in a medium, which comprises:

(i) a sensor comprising a transition metal-ligand complex containing a transition metal and at least one bi- or tri-dentate imine ligand;

(ii) an excitation light source for irradiating said sensor; and (iii) means for measuring a lifetime characteristic and/or intensity of luminescence emitted by said sensor.

BRIEF DESCRIPTION OF THE DRAWINGS

FIGS. 8(a)–(e) show the response and recovery of Os $(dppz)$ $(dppe)_2(PF_6)_2$/CM23/sol-gel water sensor in organic solvents either containing 20% $H_2O$ or $H_2O$-free.

DETAILED DESCRIPTION OF THE INVENTION

Definitions

Figure 1A:
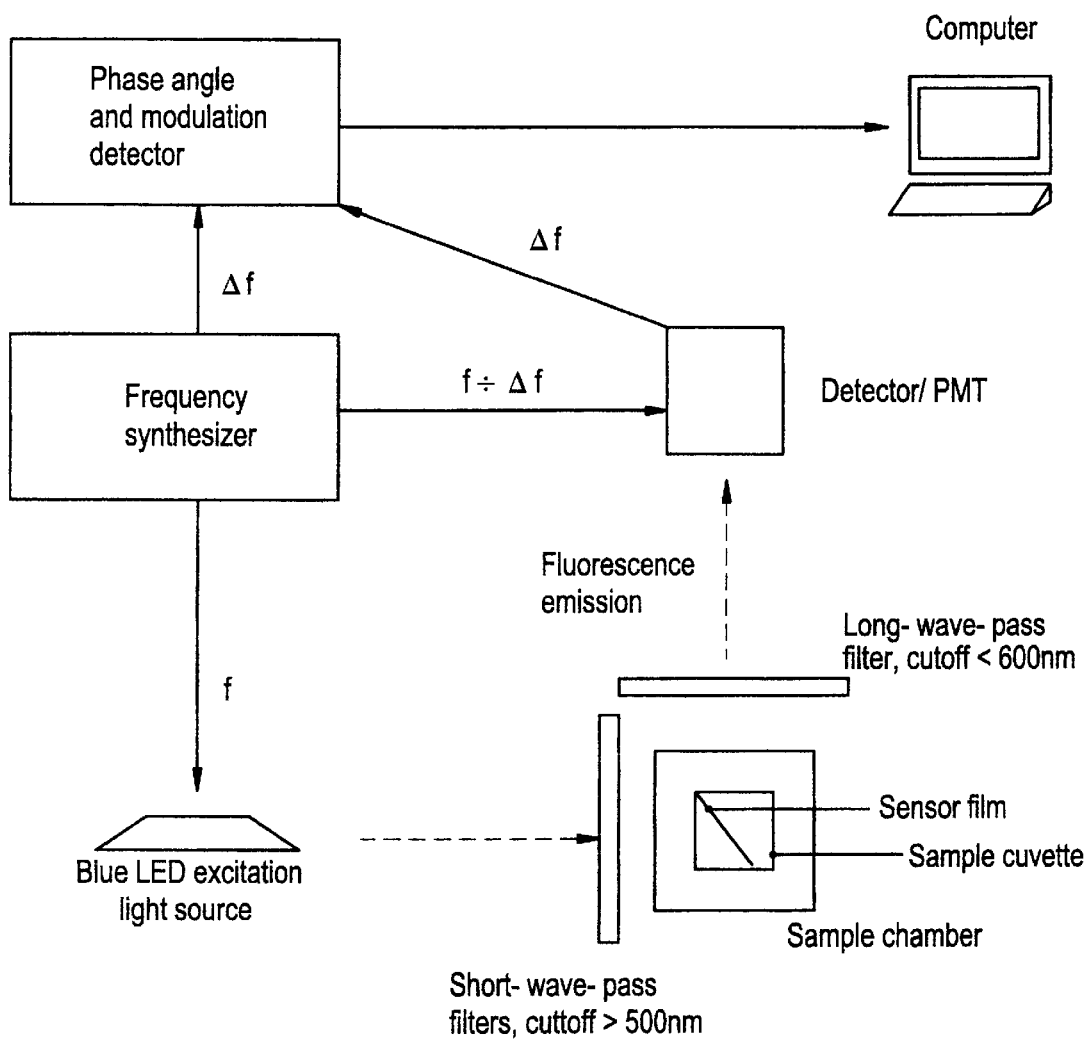
FIG. 1a schematically shows the instrumentation of phase-modulation fluorometry.

"Anion" is an atom or radical that has gained one or more electrons, and has thus acquired a negative electric charge. Suitable anions for the present invention include without limitation monoatomic and polyatomic anions such as phosphate, benzoate, carbonate, lactate, nitrate, sulfate, tartrate, glutamate, mesylate, maleate, formate, succinate, hydroxyl, chloride, bromide, iodide, fluoride and mixtures thereof.

"Luminescence" is the emission of photons from electronically excited states, which includes but is not limited to fluorescence and phosphorescence.

"Fluorescence" is luminescence which results from the return to the ground state from an excited singlet state.

"Luminescence lifetime" is the average period of time that a substance, which displays luminescence upon excitation, remains in the excited state prior to its return to the ground state.

"Phase modulation" is a method for measuring luminescence lifetime in which the sample is excited with an amplitude modulated light, and the phase angle and demodulation factor of the emission are measured and used to calculate the lifetime.

"Frequency domain" is a method for measuring the frequency response of a sample, and is similar to phase modulation fluorometry, but commonly refers to measurements at several light modulation frequencies.

"Time domain" is a method for measuring the impulse response of a sample.

"Transition metal" is any of a number of elements in which the filling of the outermost shell to 8 electrons within a period is interrupted to bring the penultimate shell from 8 to 18 or 32 electrons. These elements include elements 21 through 29 (scandium through copper), 39 through 47 (yttrium through silver), 57 through 79 (lanthanum through gold, and all known elements from 89 (actinium) on.

TRANSITION METAL-LIGAND COMPLEX

The present invention relates to a transition metal-ligand complex, which comprises:

(i) a transition metal; and (ii) at least one bi- or tri-dentate imine ligand.

In a preferred embodiment, the complex has a luminescence lifetime characteristic that changes as a function of the polarity or hydrogen bonding properties of its environment.

In another preferred embodiment, the intensity of luminescence emitted by the complex changes as a function of the polarity or hydrogen bonding properties of its environment.

In a further preferred embodiment, the complex has a structure corresponding to the formula $$M^{+n}L(X^{-Y})_z$$

wherein:

$M^{+n}$ is a transition metal cation wherein n represents the number of positive charges;

L is one to three bi- or tri-dentate ligands, at least one of which ligands is an imine;

$X^{-Y}$ is an anion wherein y represents the number of negative charges;

z is the number of anions; and the absolute value of the product of y and z is equal to n.

More preferably, M is a transition metal selected from the group consisting of ruthenium, osmium, rhenium, iridium, platinum, palladium, rhodium, copper, silver and gold; the imine is selected from diimine and triimine ligands known to yield luminescent complexes, including 2,2'-bipyridine, 4,4'-dicarboxy-2,2'-bipyridine, 4,4'-diethylaminomethyl-2,2'-bipyridine, dipyridol[3,2-a:2",3"-c]phenazine, 1,10-phenanthroline, and combinations thereof; and n is 1, 2 or 3.

Most preferably, the transition-metal ligand complex is tris(4,4'-dicarboxy-2,2'-bipyridine)ruthenium(II) hexafluorophosphate for methanol sensing, or dipyridol[3,2-a:2",3"-c]phenazine, di[cis-1,2-bis(diphenylphosphino)-ethylene]osmium(II) hexafluorophosphate for water sensing.

SENSOR

The present invention also relates to a luminescence lifetime based sensor, which comprises a transition metal-ligand complex containing a transition metal and at least one bi- or tri-dentate imine ligand. The sensor may further comprise a polymer, particularly an organic polymer such as a poly(methyl methacrylate) polymer solution.

In a preferred embodiment, the complex has a luminescence lifetime characteristic that changes as a function of the polarity or hydrogen bonding properties of its environment.

In another preferred embodiment, the intensity of luminescence emitted by the complex changes as a function of the polarity or hydrogen bonding properties of its environment.

In a further preferred embodiment, the transition metal-ligand complex has a structure corresponding to the formula $$M^{+n}L(X^{-Y})_z$$

wherein:

$M^{+n}$ is a transition metal cation wherein n represents the number of positive charges;

L is one to three bi- or tri-dentate ligands, at least one of which ligands is an imine;

$X^{-Y}$ is an anion wherein y represents the number of negative charges;

z is the number of anions; and the absolute value of the product of y and z is equal to n.

In a more preferred embodiment, M is a transition metal selected from the group consisting of ruthenium, osmium, rhenium, iridium, platinum, palladium, rhodium, copper, silver and gold; the imine is selected from diimine and triimine ligands known to yield luminescent complexes, including 2,2'-bipyridine, 4,4'-dicarboxy-2,2'-bipyridine, 4,4'-diethylaminomethyl-2,2'-bipyridine, dipyridol[3,2-a:2",3"-c]phenazine, 1,10-phenanthroline, and combinations thereof; and n is 1, 2 or 3.

For methanol sensing, the most preferred transition metal-ligand complex is tris(4,4'-dicarboxy-2,2'-bipyridine)ruthenium(II) hexafluorophosphate, or $Ru(dcbpy)_3(PF_6)_2$. Like other group six metal complexes with organic ligands (Burgess, J., Chambers, J. G., and Haines, R. I., *Transition Met. Chem.*, 1981, 6, 145), $Ru(dcbpy)_3(PF_6)_2$ displays a solvatochromic behavior, notably a solvent-dependent lifetime change in solvents with different polarity (Chang, Q., Lakowicz, J. R., and Rao, G., unpublished work). Scheme I illustrates the structure of this complex.

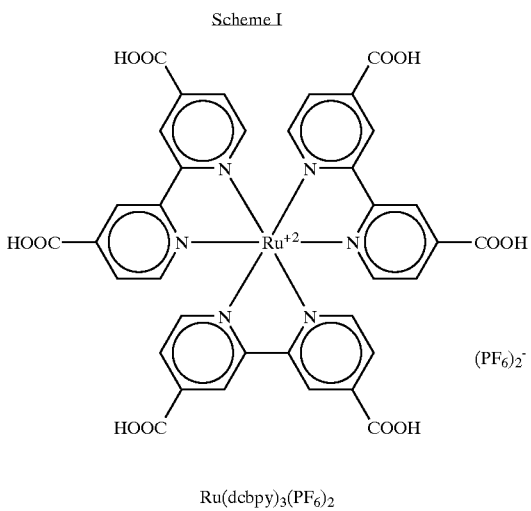

Scheme I $Ru(dcbpy)_3(PF_6)_2$

Upon acceptance of radiation energy, the complex fluoresces as a result of a metal-to-ligands charge transfer.

For water sensing, the most preferred transition-metal ligand complex is dipyridol[3,2-a:2",3"-c]phenazine, di[cis-1,2-bis(diphenylphosphino)-ethylene]osmium(II) hexafluorophosphate, or $Os(dppz)(dppe)_2(PF_6)_2$. While this complex shows significant water-dependent lifetime change, it is also sensitive to other polar molecules, such as methanol and ethanol, in mixtures with non-polar organic solvents. Scheme II illustrates the structure of this complex.

Scheme II

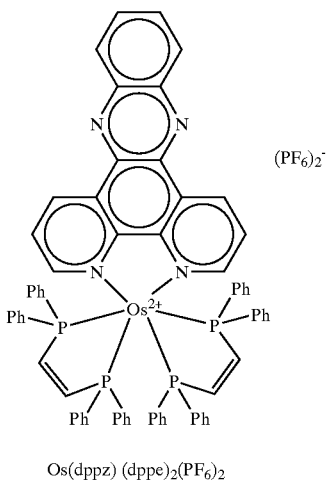

Os(dppz) (dppe)$_2$(PF$_6$)$_2$

METHODS OF USE

Additionally, the present invention relates to a method for determining the presence, amount or concentration of a polar solvent in a medium, which comprises:

(ii) determining, in the absence of the polar solvent, a luminescence lifetime characteristic of a sensor, wherein the sensor comprises a transition metal-ligand complex containing a transition metal and at least one bi- or tri-dentate imine ligand;

(iii) contacting the medium with said sensor;

(iii) determining a change in the luminescence lifetime characteristic of said sensor; and (iv) determining the presence, amount or concentration of the polar solvent in the medium based on the change in the luminescence lifetime characteristic of said sensor.

Luminescence lifetime is measured in either time domain or frequency domain. The impulse response of the system is measured in time domain, while the harmonic response of the system is measured in frequency domain.

Luminescence lifetime measurements can be performed by pulsed or time-resolved fluorometry or phase-modulation fluorometry.

In pulsed or time-resolved fluorometry, the sample is typically excited with a brief pulse of light which is preferably 10-fold shorter than the decay time of the sample. The time-dependent decay of intensity is measured either by the method of time-correlated single photon counting or by measuring the transient time-resolved luminescence itself. In either case, the time dependent values following the lamp pulse are used to calculate the lifetime. Depending on the relative magnitudes of the width of the excitation pulse and the decay time of the sample, it may or may not be necessary to deconvolute the measured luminescence decay from the pulsed excitation profile.

In phase-modulation fluorometry, the sample is excited with an amplitude modulated light, and the phase shift and demodulation of the emission, relative to the incident light, is used to calculate the luminescence lifetime.

In a preferred embodiment of the present method, the luminescence lifetime characteristic is measured in time domain using pulsed or time-resolved fluorometry. Under this method, a luminescent sample is illuminated with a narrow pulse of light and the resulting luminescence emission decay is recorded. The decay profile may be reconstructed using time correlated single photon counting. This technique involves recording the time delay between the emitted photon and the excitation pulse, and plotting the delay time against the number of photons. To properly reconstruct the decay curve, the excitation profile should also be measured to deconvolve the finite width of the excitation pulse from the emission profile.

In another preferred embodiment, the luminescence lifetime characteristic is measured in frequency domain using phase-modulation fluorometry. Lakowicz, J. R., *Principles of Fluorescence Spectroscopy*, Plenum Press, New York, 1983; Lippitsch, M. E., and Draxler, S., Sens. Actuators B, 1993, 11, 97. FIG. 1a schematically illustrates the instrumentation based on this methodology. A modulated excitation light source is used, which forces the emission light of the indicator fluorophore to also be modulated, but with a lifetime-dependent delay in phase angle and decrease in modulation. These phase angle and modulation changes can be detected at a low frequency through cross-correlation by modulating the gain of the photomultiplier tube (PMT) at a frequency different by Df from the frequency of the incident light. While cross-correlation detection is desirable, it is not essential to practice the present invention.

For a single exponential decay, the phase angle shift, f, and the demodulation factor, m, are related to the lifetime of the fluorophore by the following equations:

$$\tan f = w t_p \qquad (1)$$

$$m = (1 + w^2 t_m^2)^{-1/2} \qquad (2)$$

wherein w=2p× (frequency of excitation light), and $t_p$ is the lifetime obtained from the measured phase angle, which is equal to $t_m$, the lifetime from the demodulation factor.

For a multi-exponential decay or non-exponential decay, the apparent lifetimes are only interpretations of the measured values of f and m (Lakowicz, J. R., *Principles of Fluorescence Spectroscopy*, Plenum Press, New York, 1983), and are no longer equal to each other. The relationship between phase angle, demodulation factor, and these apparent lifetimes are more complicated. One is referred to Lakowicz, J. R., *Principles of Fluorescence Spectroscopy*, Plenum Press, New York, 1983, for more details. In general, an increase in phase angle and a decrease in modulation reflect a lifetime increase. Since phase angle is insensitive to the geometry of a solid sample, it is a more reliable parameter to represent lifetime.

An alternative method for determining the presence, amount or concentration of a polar solvent in a medium, comprises:

(i) determining, in the absence of the polar solvent, the intensity of luminescence emitted by a sensor, wherein the sensor comprises a transition metal-ligand complex containing a transition metal and at least one bi- or tri-dentate imine ligand;

(iii) contacting the medium with said sensor;

(iii) determining a change in the luminescence intensity of said sensor; and (iv) determining the presence, amount or concentration of the polar solvent in the medium based on the change in the luminescence intensity of said sensor.

Preferably, luminescence intensity is measured in time domain using pulsed or time-resolved fluorometry.

The polar solvent whose presence, amount or concentration is determined by the above methods may be an alcohol, glycol or similar molecule. Examples of such polar solvent include, without limitation, water, methanol, ethanol, propanol, butanol, ethylene glycol and N-methylacetamide. The preferred polar solvents are methanol and water.

PROBE

The sensor may be attached to an optical substrate which serves as an optical waveguide. In this manner, luminescence exciting radiation can be transmitted to the sensor, and emitted luminescence radiation can be carried away from the sensor to a detector. A single optical waveguide can be utilized for both transmission of the excited radiation to the sensor and transmission of luminescence emitted by the sensor to the detector. Alternatively, more than one optical waveguide can be utilized, with at least one optical waveguide to transmit luminescence exciting radiation to the sensor, and at least one other optical waveguide to transmit emitted luminescence away from the sensor.

In a preferred embodiment, the optical waveguide is an optical fiber. When an optical fiber is used as the optical waveguide, the sensor and optical waveguide assembly is collectively referred to as a probe.

SYSTEM

When the sensor is combined with other elements, such as an excitation light source for irradiating the sensor, and means for measuring a lifetime characteristic and/or intensity of luminescence emitted by the sensor, the resulting assembly is collectively referred to as a system. The sensor may be attached to the other elements either directly or by way of one or more optical waveguides. For example, the sensor may be attached to at least one optical waveguide, which in turn is attached to an excitation light source for irradiating the sensor and means for measuring a lifetime characteristic and/or intensity of luminescence emitted by the sensor. In a preferred embodiment, the system comprises a cuvette containing a sensor in combination with an excitation light source and a detector.

Any excitation light source may be used to irradiate the sensor. Examples of a suitable light source include incandescent sources, arc lamps, lasers and light emitting diodes (LEDs). As mentioned in Sipior, J., Bambot, S., M., Romauld, Carter, G. M., Lakowicz, J. R., and Rao, G., *Anal. Biochem.*, 1995, 227, 309 and Chang, Q., Sipior, J., Lakowicz, J. R., and Rao, G., *Anal. Biochem.*, 1995, 232, 92, and demonstrated in Sipior, J., Randers-Eichhorn, L., Lakowicz, J. R., Carter, G. M., and Rao, G., *Biotechnol. Prog.*, 1996, 12, 266, an inexpensive LED is used if the lifetime of the fluorophore is long enough such that phase-modulation can be measured in a modulation frequency of 0.05–25 MHz—the typical frequency range at which an LED can be modulated fairly well. The use of an LED eliminates the need for an expensive laser light source, and subsequently the need for an RF amplifier and a Pockels cell modulator.

If the excitation light source does not already produce monochromatic light, it will be necessary to include one or more filters or monochromators to render the light monochromatic. Luminescence emitted by the fluorophore in the sensor will generally be rendered monochromatic in a similar manner by use of a monochromator with or without various filters to eliminate scattered light, or a beam splitter combined with one or more filters to produce two beams at different wavelengths.

A detector is used to collect and measure the emitted luminescence. Examples of a suitable detector for the present invention include photomultipliers, semi-conductor devices such as photodiodes, and position sensitive detectors. In a preferred embodiment, the detector is capable of comparing luminescence signals from a sensor in contact with a sample and a reference sensor. If changes in the luminescence emission are used to detect a physical or chemical characteristic of a sample, the detector should be capable of comparing the luminescence intensity in at least two wavelengths, either simultaneously or sequentially. Alternatively, if the luminescence lifetime of a sample is used for detection, the detector would only need to measure luminescence intensity at a single emission wavelength.

In addition to the above devices, the system may further include analog and digital circuitry to collect and analyze data. In all cases where specific devices have been mentioned in this application, their functional equivalents are also contemplated.

EXAMPLES

The following examples are illustrative of the present invention and are not intended to be limitations thereon. Unless otherwise specified, all the measurements were performed at ambient temperature.

Example I

Preparation of Film Sensor

A film sensor was prepared using a method similar to that described in Hubert, C., Fichou, D., Valat, P., Garnier, F., and Villeret, B., *Polymer*, 1995, 36, 2663.

First, $Ru(dcbpy)_3(PF_6)_2$ was synthesized as follows. $RuCl_3$ (0.1 g) and 2,2-bipyridine-4,4'-dicarboxylic acid (3.67 g) were suspended in 15 ml of ethylene glycol and refluxed for 2 hours. The solution was cooled to room temperature and filtered. After the addition of 2.5 g $NaPF_6$ in 25 ml $H_2O$, the pH of the filtrate was adjusted to 1.0 with concentrated $H_2SO_4$ and the solution was cooled for a few hours. The precipitate was collected and resuspended in MeOH, filtered and dried over $P_4O_{10}$. Yield: 0.38 g (68%). Kalyanasundaram et al., "Synthesis and photophysical characterization of highly luminescent complexes of Ru(II) containing 4,4'-di-(p-carboxyphenyl)-2,2'-bipyridine", *Inorg. Chim. Acta.*, 1992, 198–200, 831–839.

Next, a polymer solution, solution I, was prepared by dissolving 15 mg of PMMA (average MW: 996,000) in 1 ml of dichloromethane (99.8%, anhydrous) (DCM). 0.3 mg of $Ru(dcbpy)_3(PF_6)_2$ was then dissolved in 0.25 ml of methanol (99.9+%, HPLC grade) to form solution II. 0.15 ml of solution II was added and mixed into solution I to form solution III, the solution used for the sensing film casting. 20 ml of solution III was spread onto a piece of quartz glass slide (12.5 mm×15 mm). Upon drying at room atmosphere, solution III formed into a clear and transparent film. It is noted that a turbid film would have resulted if the content of methanol in solution III was too high. To avoid this situation, a mixture of methanol and DCM could be used as the solvent for solution II to reduce the methanol content in solution III.

Example II

Measurement of Fluorescence Excitation and Emission Spectra

The fluorescence excitation and emission spectra were measured using an ISS K2 Multifrequency Phase and Modulation Fluorometer (Champaign, Ill.), and a xenon arc lamp with band-passes of 8 nm and 16 nm for the excitation and emission monochromators, respectively.

Figure 2:
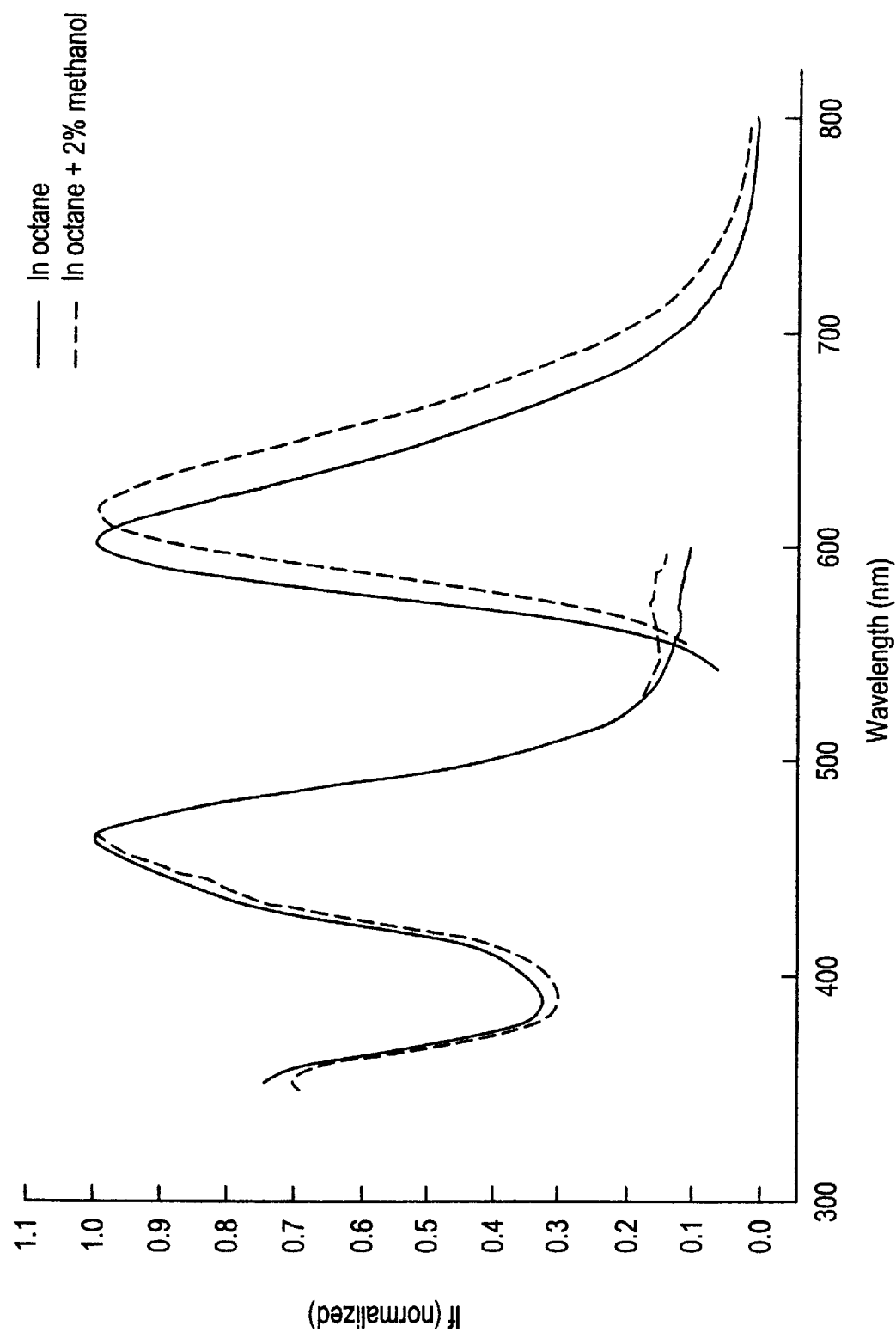
FIG. 2 shows the normalized excitation and emission spectra (un-corrected) of $Ru(dcbpy)_3(PF_6)_2$/PMMA film sensor in octane and octane with 2% methanol.

FIG. 2 shows the excitation and emission spectra of Ru(dcbpy)$_3$(PF$_6$)$_2$ in PMMA polymer film. The solid lines represent the spectra measured in octane (>99.5%, Optima), while the dashed lines represent the spectra measured in a mixture of 2% methanol in octane. When the solution was changed from octane to 2% methanol in octane, the solvent polarity increased. Both of the excitation and emission spectra were found to display a positive solvatochromism, i.e. a bathochromic (or red) shift with increasing solvent polarity. The small bathochromic shifts of 4 nm for the excitation spectra and 18 nm for the emission spectra indicate a small increase in dipole moment of the ruthenium compound from its ground state to its excited state. This is expected because the symmetric structure of the compound (see Scheme I) allows the metal-to-ligand charge transfer (Demas, J. N., and DeGraff, B. A., *Anal. Chem.*, 1991, 63, 829A) to happen in a roughly spherical fashion, whereby little overall dipole change is produced.

As described by the Lippert equation (Lakowicz, J. R., *Principles of Fluorescence Spectroscopy*, Plenum Press, New York, 1983), large absorption or emission spectrum shift generally results from a large dipole moment change of a compound when going from the ground state to the excited state. This dipole moment change interacts strongly with the solvent dipoles and causes large solvent effects on state energies and spectra. Although a compound showing a large dipole moment difference between the ground and excited states produces large solvent effects on state energies and spectra, such compound does not necessarily produce a large solvent effect on lifetime.

While more examples can be found, for instance, in Reichardt, C., *Solvent and Solvent Effects in Organic Chemistry*, VCH Publishers, New York, 2nd edn., 1988, the preferred compound used by the inventors for exemplification was 1-phenyl-4-(4-cyano-1-naphthyl-methylene) piperidine. The dipole moment of this compound increases about 17 times from 5×10$^{-30}$ Cm in the ground state to 83×10$^{-30}$ Cm in the excited state. When measured in solvents of n-hexane, benzene, chloroform, dichloromethane, and pyridine in the order of increasing solvent polarity, the compound displayed similarly increasing bathochromic shifts in the emission maxima of 412, 478, 531, 579 and 627 nm, respectively, but disordered lifetimes of 1.2, 15, 13, 9 and 1 ns, respectively. This indicates that a good spectrum-dependent solvatochromic indicator is not necessarily a good lifetime-dependent solvatochromic indicator, and vice versa.

In their studies, the inventors focused mainly on the solvent-dependent lifetime change. Among a number of ruthenium compounds, Ru(dcbpy)$_3$(PF$_6$)$_2$ exhibited the largest lifetime difference in chloroform and in methanol. Therefore, despite its small spectral shift, this compound was selected as the lifetime-based solvatochromic probe.

Example III–VII

Measurement of Fluorescence Phase-Modulation

Figure 1B:
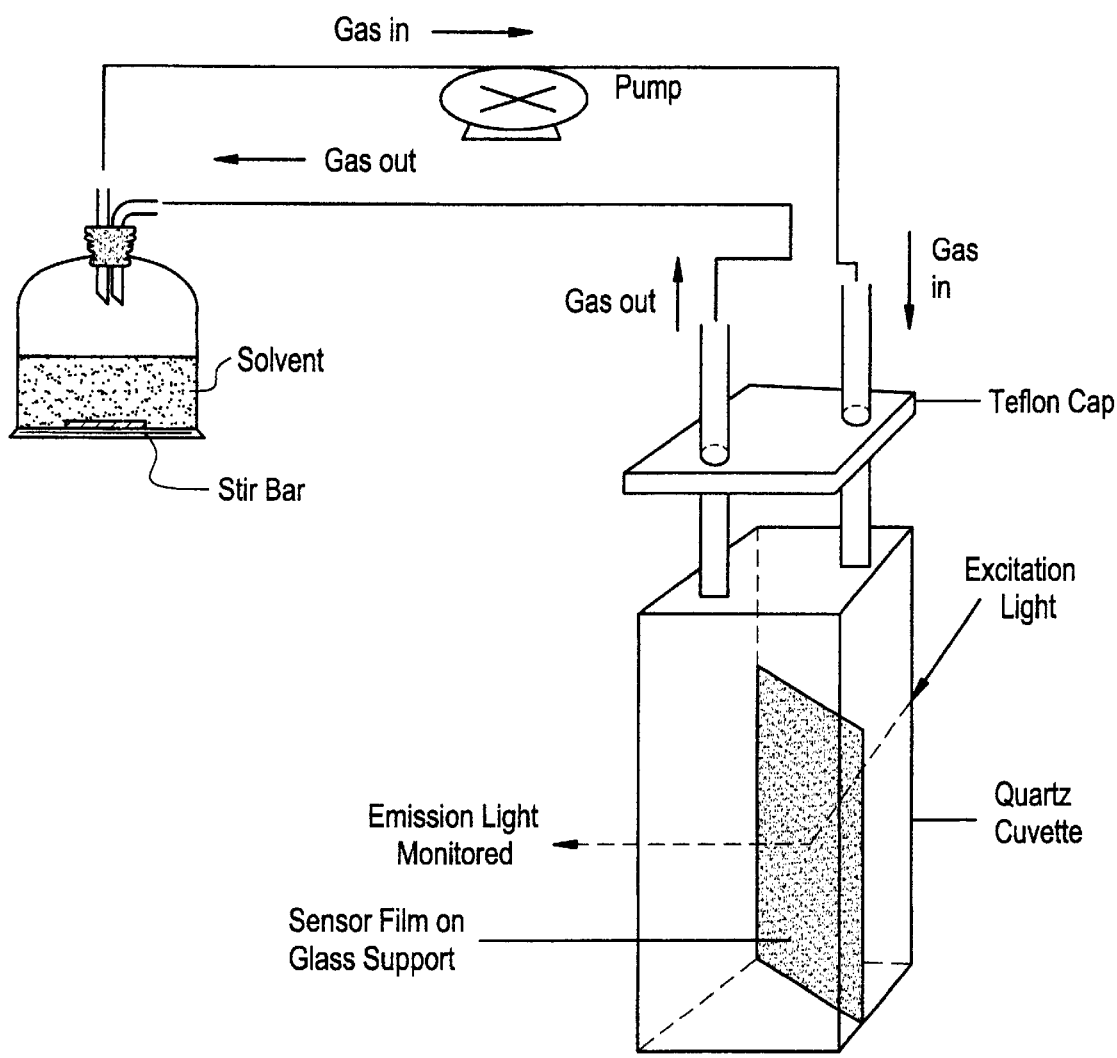
FIG. 1b schematically shows the experimental setup used in the lifetime measurements of the film sensor in gas phase.

Fluorescence phase-modulation was measured using an ISS K2 Multifrequency Phase and Modulation Fluorometer (Champaign, Ill.), and a blue LED (NLPB500, Nichia America Co., Lancaster, Pa.) with an emission maximum of around 450 nm. Light from the LED with a wavelength of more than 500 nm was cut off by placing a set of short wave-pass filters (500FL07, 600FL07 and 700FL07, Andover, Salem, N.H.) in the excitation path. The fluorescence was collected through an Andover 600FH90 long-wave-pass filter which cut off all the light below 600 nm to prevent scattered light from coming through. The lifetime reference solution used in the measurements was a 0.5% solution of Du Pont Ludox HS-30 colloidal silica in water. Its scattered light intensity was adjusted by adding proper neutral density filter(s) in its emission path to match the emission light intensity from the film sensor. The film sensor supported on the quartz glass slide was fixed in a quartz fluorescence cuvette at an orientation of about 60° to the excitation light beam. See FIG. 1b.

Liquid Phase Measurements

Example III

Dependence of Phase Angle and Modulation on Methanol Concentration

For liquid phase measurements, 3 ml of octane or a mixture of a certain percentage of methanol in octane was pipetted into the cuvette, and the phase angle and modulation were measured approximately 10 minutes later. After each measurement, the used solution was withdrawn with a glass disposable pipet, and a new solution was injected into the cuvette when necessary.

Figure 3:
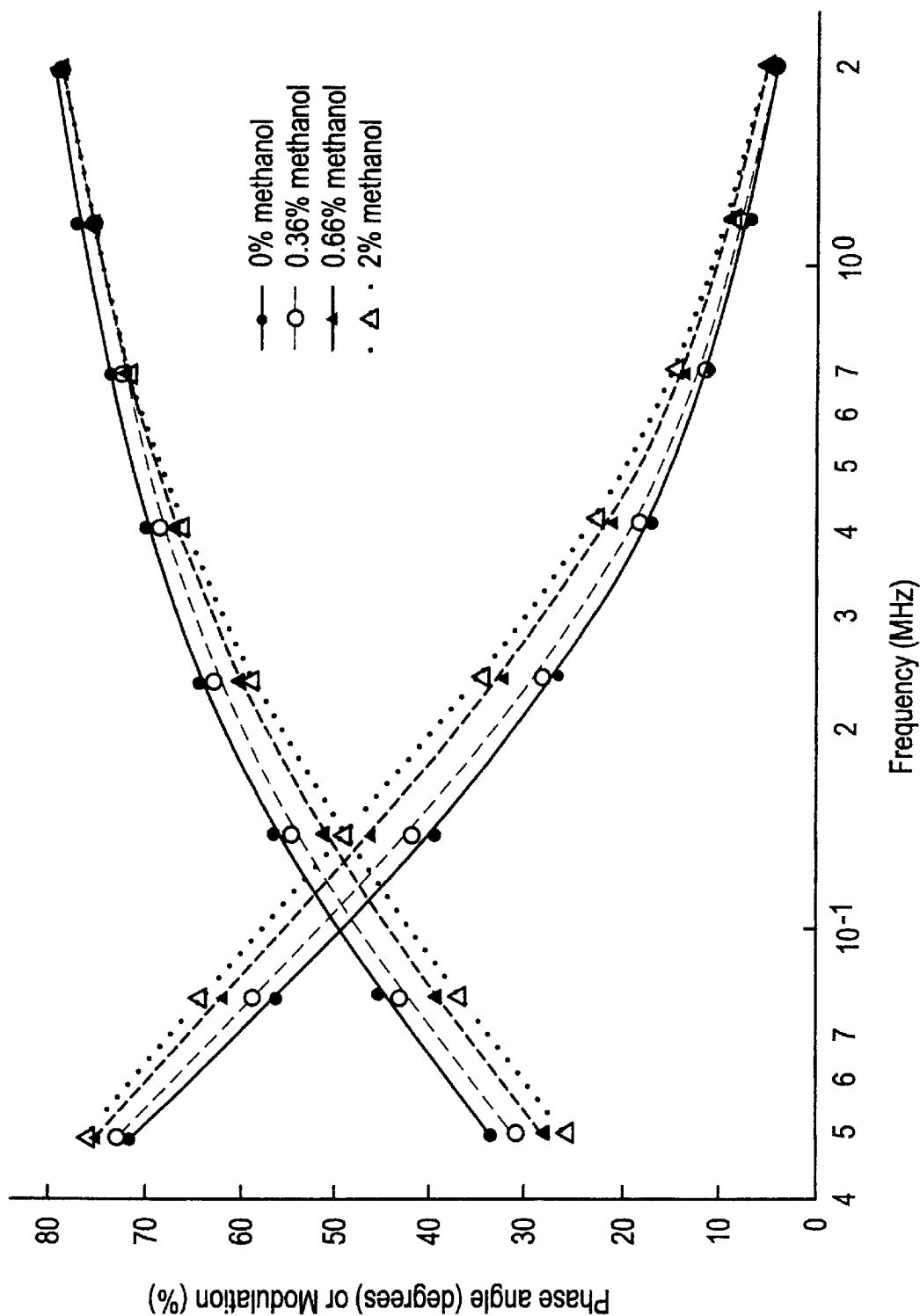
FIG. 3 shows the dependence of the phase angle and modulation (and therefore, the lifetime) on the concentration of methanol in octane.

FIG. 3 shows the dependence of the phase angle and modulation (and therefore, the lifetime) on the concentration of methanol in octane. The phase angle decreased and the modulation increased, when methanol concentration increased. Such results were particularly evident at modulation frequencies below 500 KHz, indicating a decrease in the lifetime of the ruthenium compound.

Figure 4:
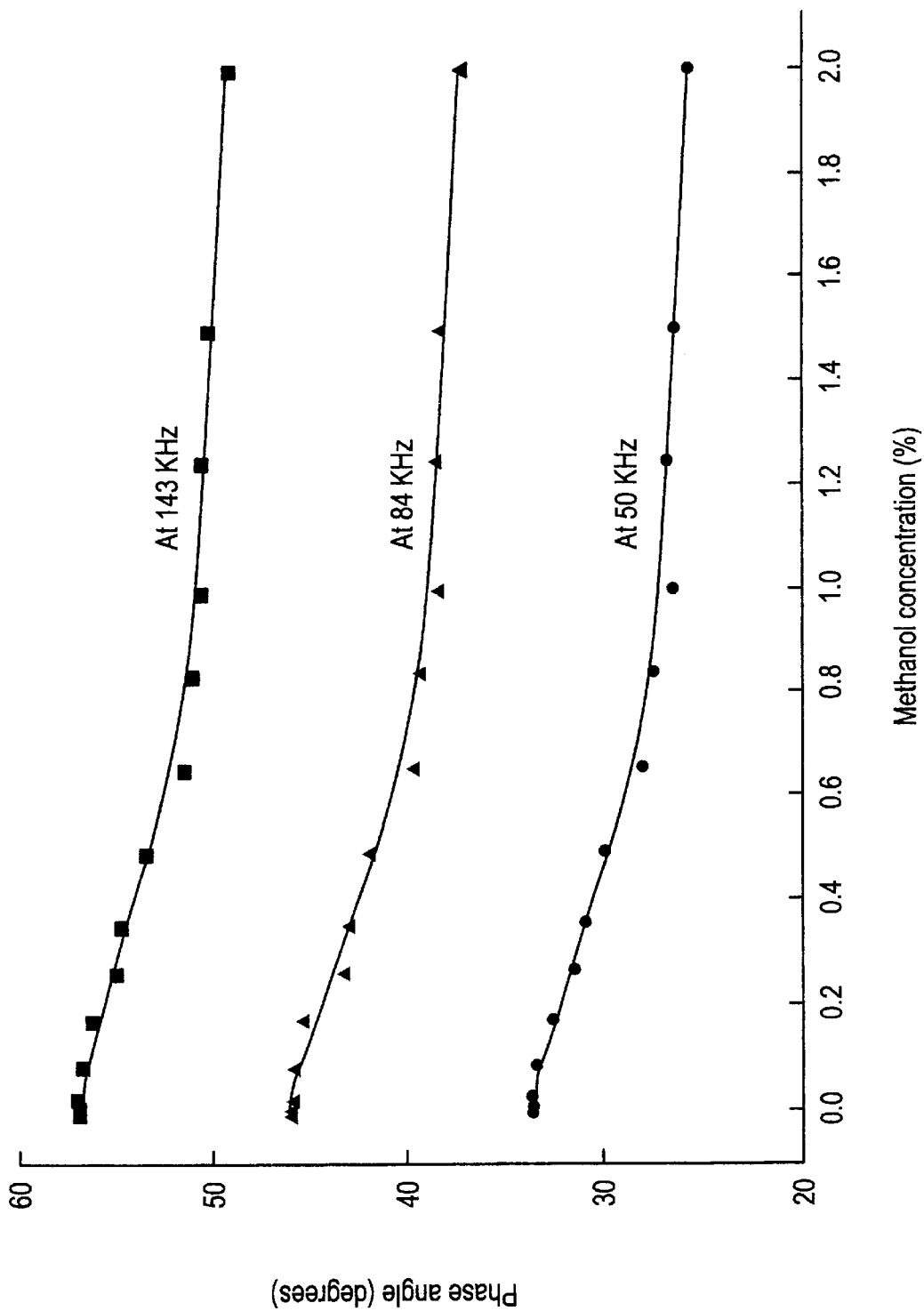
FIG. 4 shows phase angle as a function of the concentration of methanol in octane, as measured under the conditions specified in FIG. 3 at frequencies of 0.05, 0.084 and 0.143 MHz.

At frequencies of 50, 84 and 143 KHz, an increase in methanol concentration from 0 to 2% in octane caused a phase angle decrease of about 7.7°, 8.8° and 7.6°, respectively. FIG. 4 shows these methanol-dependent phase angle changes. The most sensitive range of phase angle to methanol concentration fell between 0.09% and 0.7%, with a slope of approximately −9°/1%. Since the phase angle can be detected at an accuracy of 0.1° to 0.2° with a better phase detector, a measurement resolution of 0.01–0.02% of methanol in this range may be assumed. Furthermore, by choosing an appropriate matrix, it would be possible to construct sensors that are sensitive to different ranges of solvent polarity. Because a solution containing 3% methanol induced cracking of the PMMA film, the response of the film sensor to a solution with methanol concentration higher than 2% was not investigated.

Example IV

Time-Dependent Response and Recovery of Film Sensor to Menthanol

The film sensor was placed in a cuvette containing only octane. After a while, the solution was carefully withdrawn from the cuvette using a glass disposable pipet, which was followed by an immediate injection of 3 ml of 2% methanol in octane. This produced a phase angle decrease of about 8°. The response time for 95% of the total signal to change, $t_{95\%}$, was worked out as 22 seconds. When the reading was steady, using the same method as described above, the 2% methanol in octane was withdrawn and fresh octane was added. This procedure was repeated for another cycle.

Figure 5:
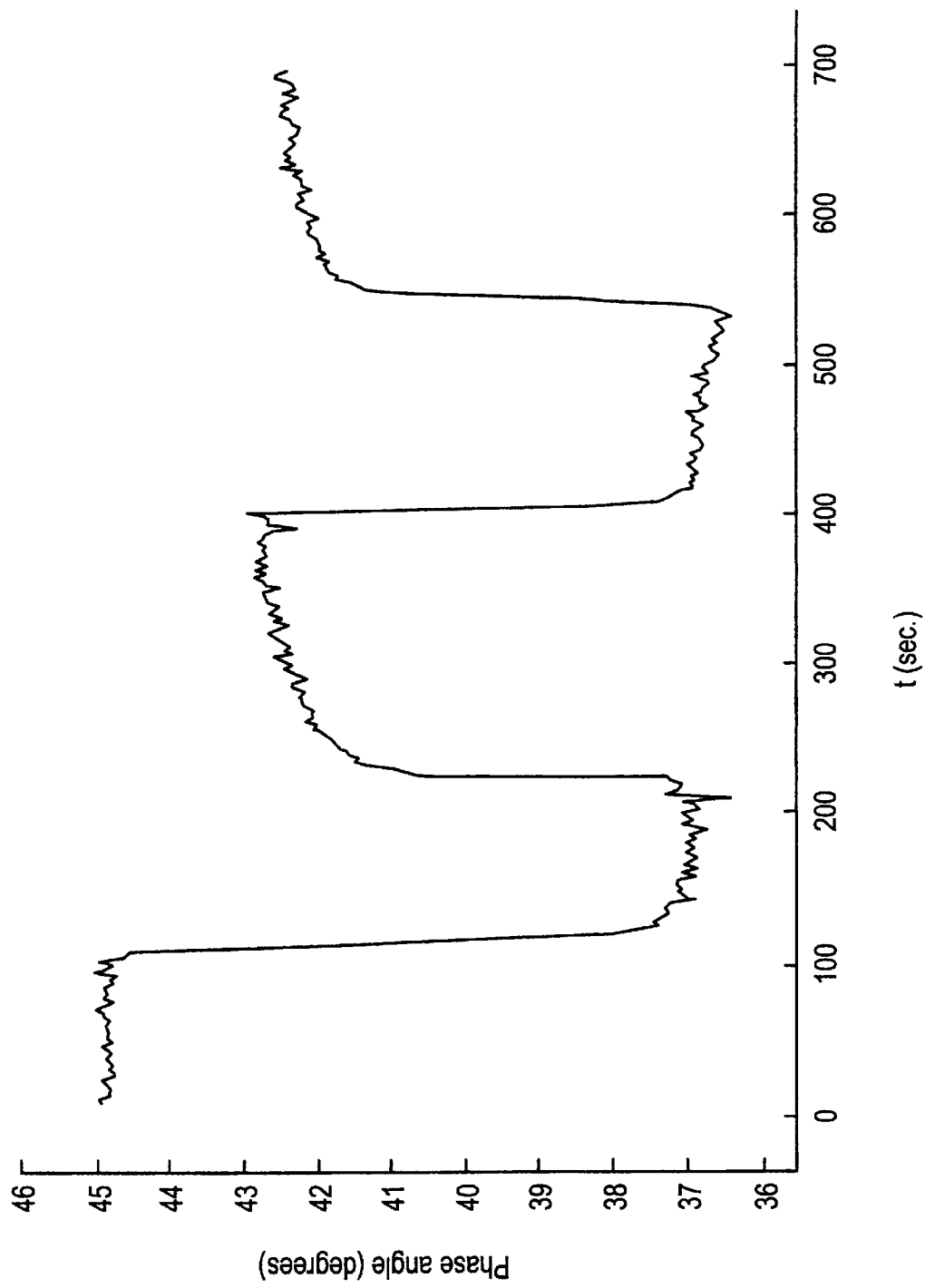
FIG. 5 shows time-dependent response and recovery behavior of $Ru(dcbpy)_3(PF_6)_2$/PMMA film sensor, as monitored at 0.084 MHz and under the conditions specified in FIG. 3.

FIG. 5 shows the time-dependent response and recovery of the film sensor to methanol. The incomplete recovery of the film sensor was probably due to the residual methanol left within the matrix after the withdrawal of the methanol solution. The partial recovery was not permanent because, in the study of the long-term stability of the film sensor (see FIG. 6), the inventors found that the film sensor fully recovered when left overnight.

Example V

Long-Term Stability of Film Sensor

Figure 6:
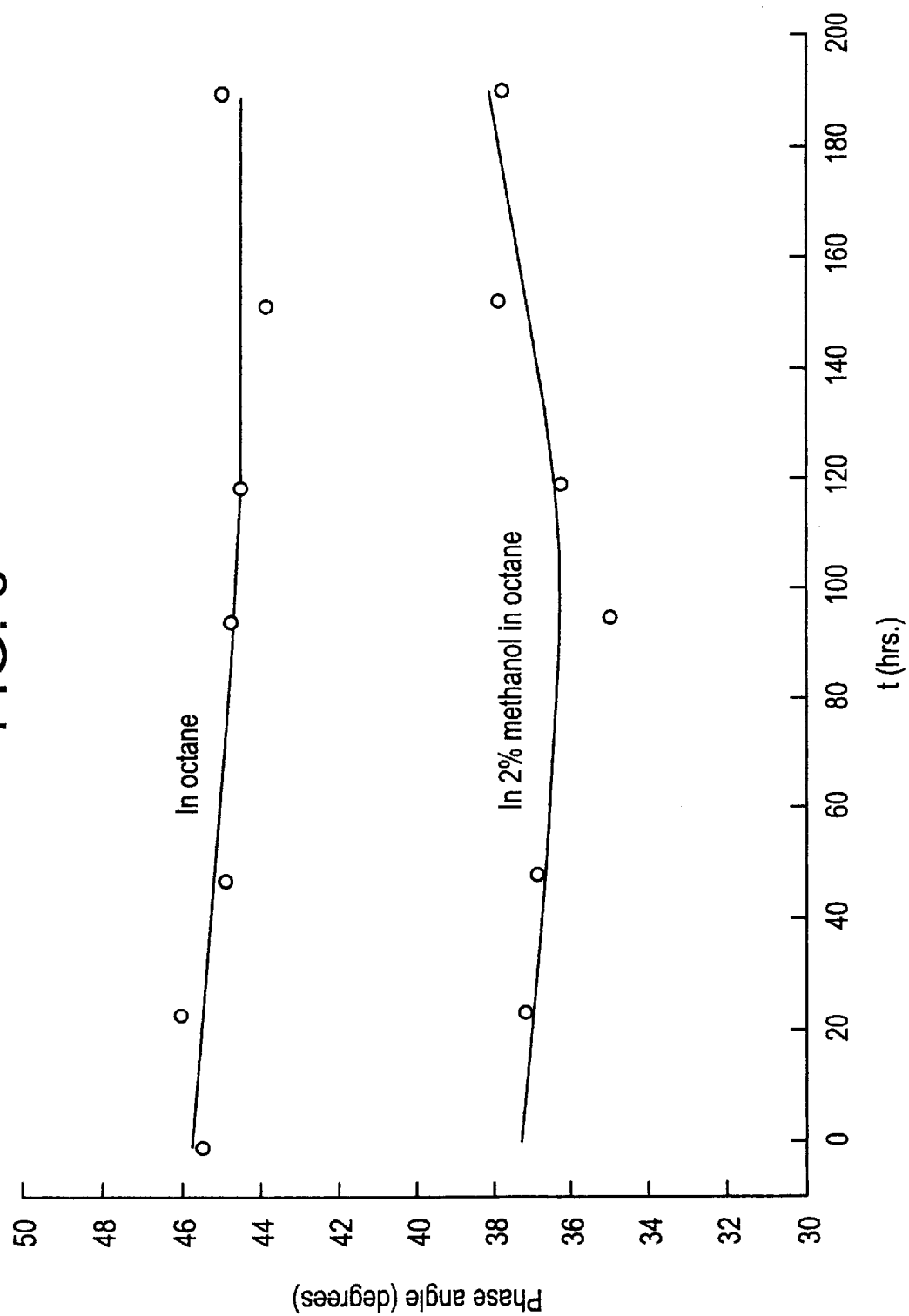
FIG. 6 shows long-term stability of $Ru(dcbpy)_3(PF_6)_2$/PMMA film sensor, as monitored at 0.084 MHz and under the conditions specified in FIG. 3.

The phase angle of the film sensor was measured at 84 KHz in octane and 2% methanol in octane on a daily basis. After each set of measurements, the solution was completely removed, and the film sensor was left in room atmosphere until measurements were taken the following day. The phase angle in both octane and 2% methanol in octane appeared to have slowly shifted with time. After initial use, the film sensor remained useful for at least 5–6 days. FIG. 6 shows the long-term stability of the film sensor.

Example VI

Dye Wash-Out

To detect dye wash-out, a film sensor was placed in a solution of 2% methanol in octane for one hour, then removed, and the fluorescence intensity of the remaining solution was measured. Under the same condition of the instrumentation for lifetime measurements, the measured intensity was only about 0.4% of the quenched intensity from the film sensor in the methanol containing mixture, and about 0.2% of the unquenched intensity in octane, which was close to the noise level from the background of the measurement setup. Thus, the inventors did not find any evidence of dye wash-out based on the measured fluorescence intensity of the 2% methanol in octane solution. The inventors also did not detect a continuous decrease in the fluorescence intensity from the film sensor, another evidence of dye wash-out.

Gas Phase Measurements

Example VII

For the potential use of the sensor in fermentation and other gas phase applications, the response of the sensor to a number of solvent vapors in gas phase was studied. Pure nitrogen and compressed air were delivered directly from gas supply sources, while the other gases of solvent vapor saturated in air were produced in the vapor phase of a solvent container, and circulated into the cuvette by a circulation pump (MasterFlex, Model 7520-10, Cole-Parmer, Chicago, Ill.). A schematic illustration of the setup is given in FIG. 1b.

Figure 7:
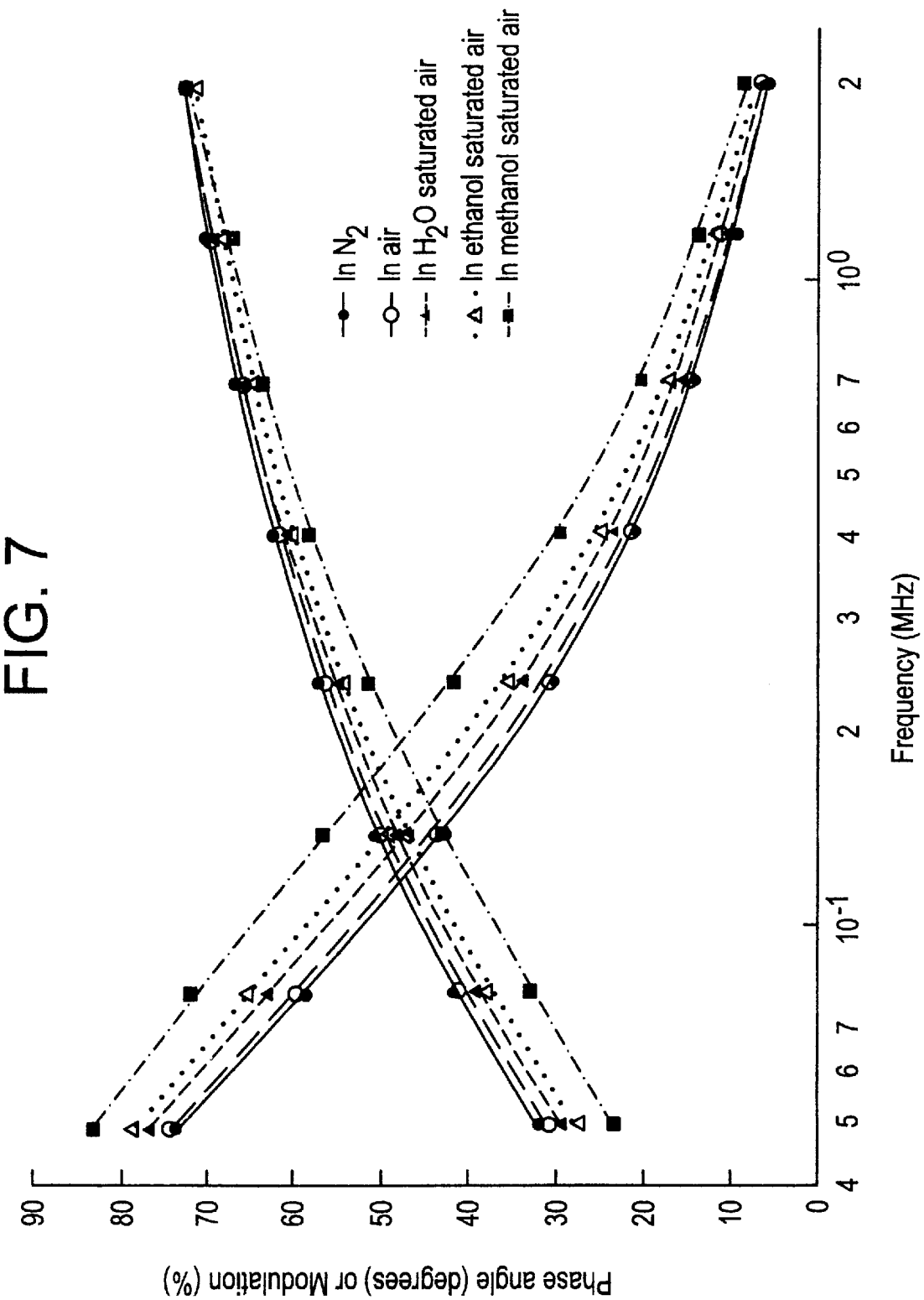
FIG. 7 shows $Ru(dcbpy)_3(PF_6)_2$/PMMA film sensor in various gas phase environment, as monitored under the conditions specified in FIG. 3.
Figure 8A:
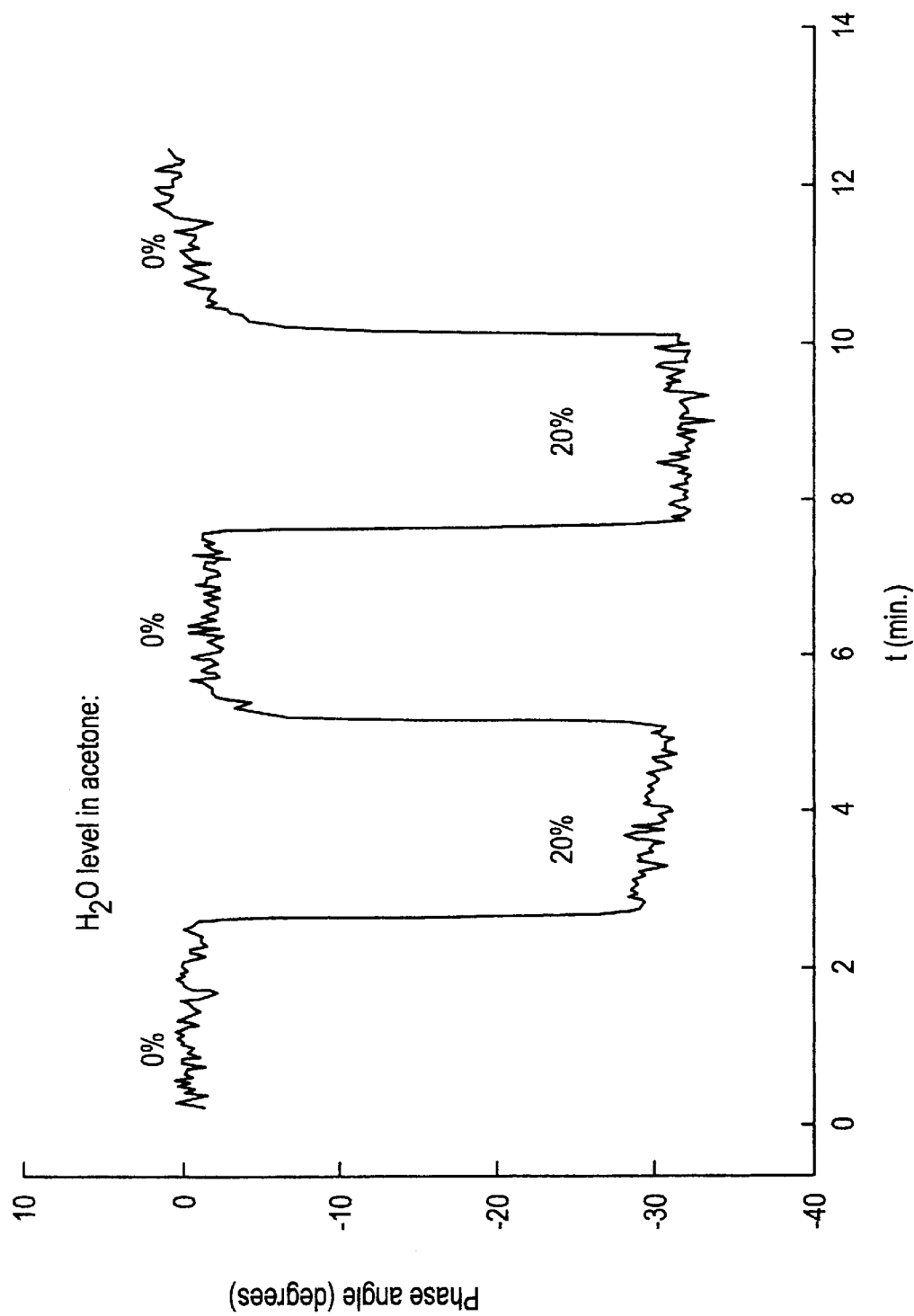
Figure 8B:
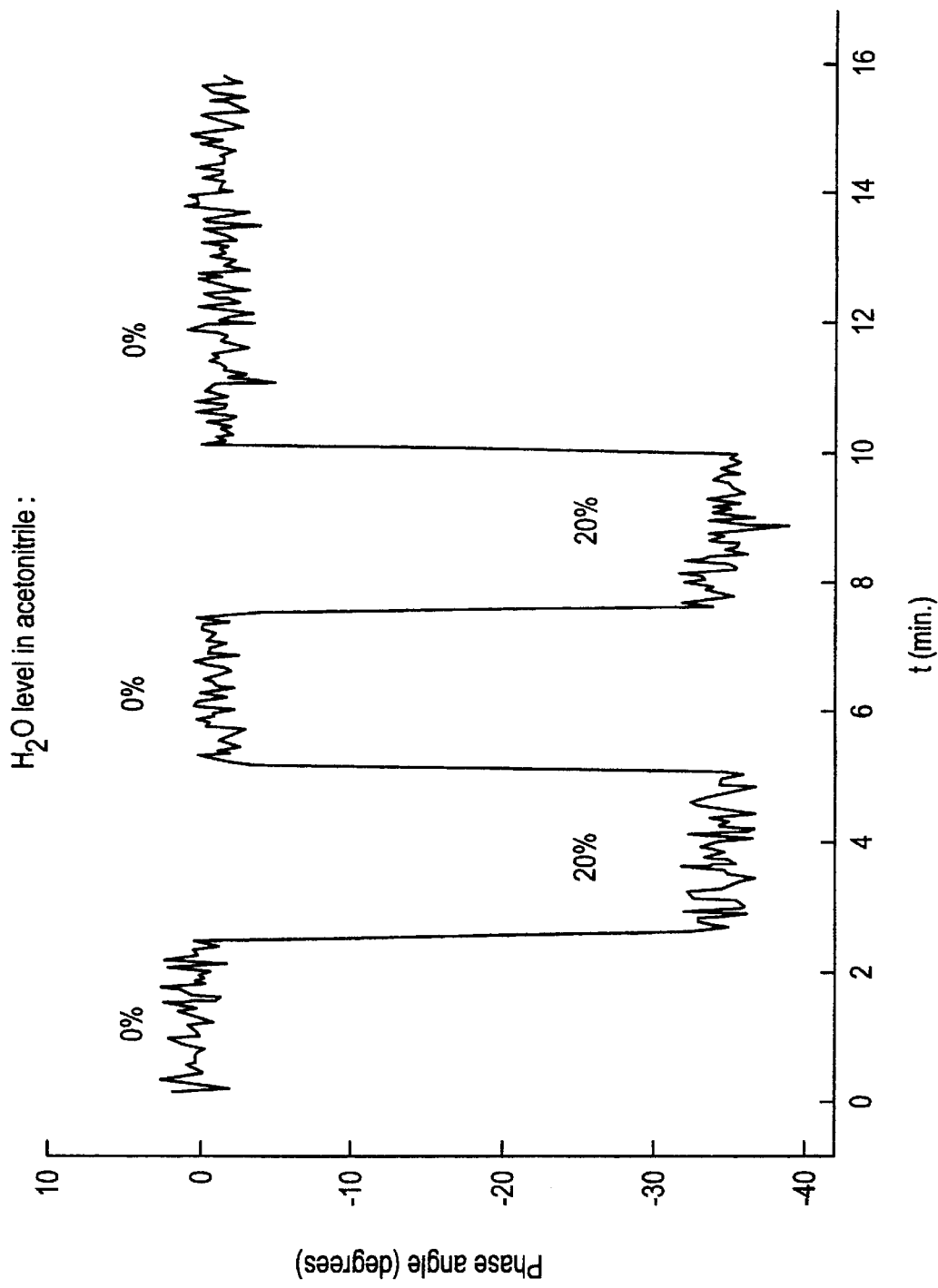
Figure 8D:
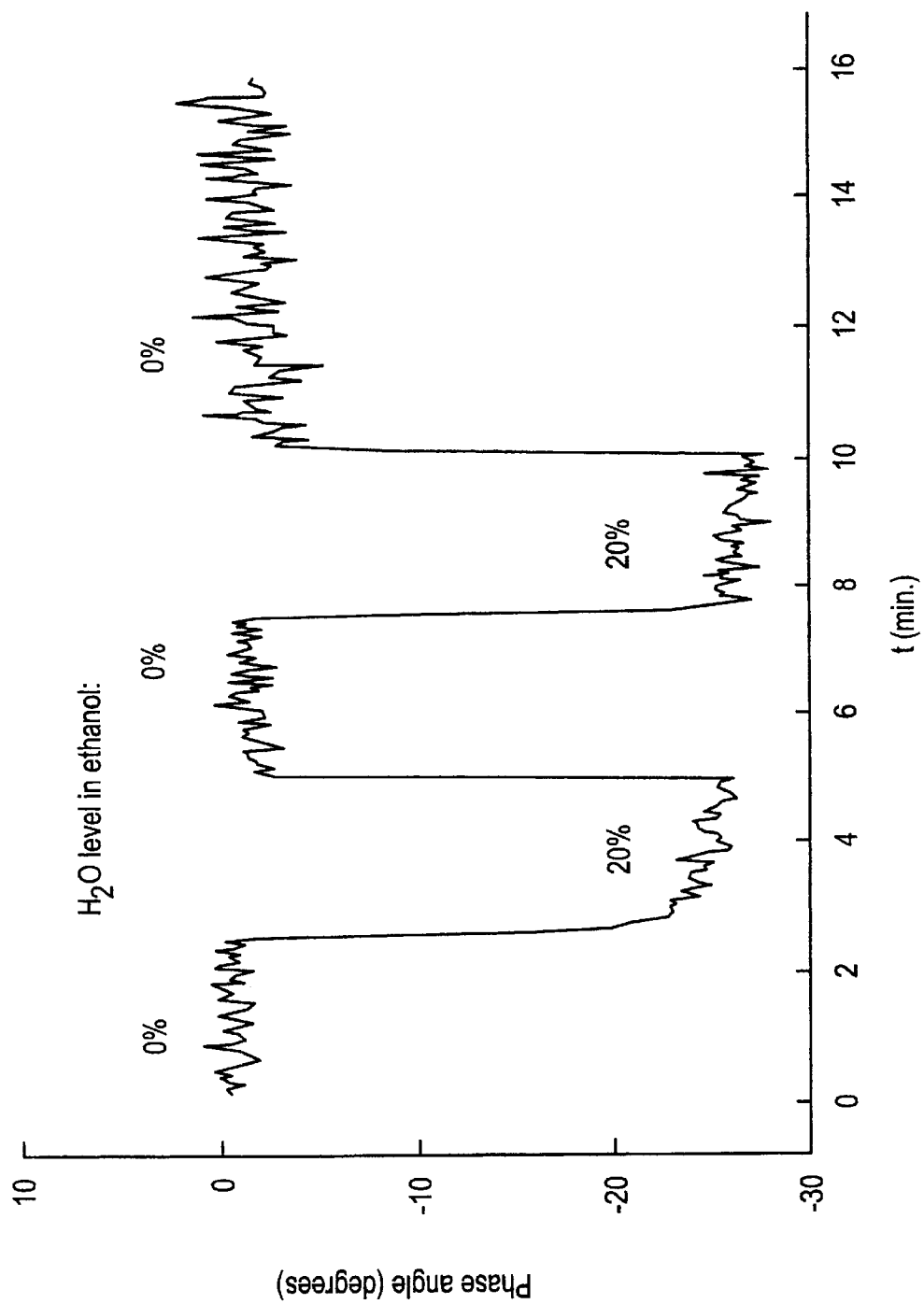

As shown by the long-dashed lines in FIG. 7, oxygen in the air had minor quench effects on the lifetime of the ruthenium compound. Although most ruthenium complexes with α-diimine ligand, such as 2,2'-bipyridine, are subject to oxygen quenching (Cook, M. J., Lewis, A. P., McAuliffe, G. S. G., Skarda, V., Thomson, A. J., Glasper, J. L., and Robbins, D. J., *J. Chem. Soc.* Perkin Trans. II, 1984, 1293), the degree of this effect in the inventors' studies is low in the PMMA matrix. In previous studies on a lifetime-based $NH_3$ sensor (Chang, Q., Sipior, J., Lakowicz, J. R., and Rao, G., *Anal. Biochem.*, 1995, 232, 92), the inventors also noted that oxygen had little influence on the lifetime of sulforhodamine 101 dissolved in ethyl cellulose polymer film. Because of the limited solubility of oxygen in these polymers, the polymer matrixes provide a significant advantage for fluorescence-based sensing where the interference of oxygen is a common, inevitable problem. While the short-dashed lines in FIG. 7 indicate that humid air has some effect on the lifetime of the ruthenium compound, the predominant response of the film sensor to the methanol vapor saturated in air (dot-dashed lines) remained clear. This supports the use of the sensor for monitoring methanol in fermentation. The sensor appeared less sensitive to ethanol (USP pure grade) vapor (dotted lines) than methanol vapor. This result is consistent with ethanol's less polar nature, when compared to methanol.

Example VIII

Preparation of Water Sensor

First, the metal-ligand complex Os (dppz) $(dppe)_2(PF_6)_2$ was loaded onto carboxymethyl cellulose, or CM23 (Fisher Scientific). Specifically, 4.4 mg of CM23 was added into 0.5 ml of $3.2 \times 10^{-3}$ M Os(dppz) $(dppe)_2(PF_6)_2$ in a 1:1 (v:v) mixture of acetone and water, whereby a suspension formed. The suspension was then shaken, and after standing overnight, centrifuged. The resulting powder which separated from the solution was washed with 1:1 (v:v) acetone and water many times until the supernatant liquid appeared colorless. The powder was dried in a 60° C. oven, and then suspended in 0.2 ml of methanol. 10 μl of the resulting suspension was spread onto a side-wall of a flow cell (12 mm×10 mm). Upon drying, the suspension formed into a thin layer of Os-complex/CM23.

Next, the sol-gel solution was prepared by adding 0.66 ml of methanol, 0.22 ml of D.I. water, 30 μl of N,N-dimethyl formamide (Aldrich) and 30 μl of ammonia solution (pH 11.2) into 0.5 ml of tetramethylorthosilicate (Aldrich).

The resulting sol-gel solution was left to stand for 2 minutes, following which 10 μl of the solution was applied onto the thin layer of Os-complex/CM23. After being left overnight in ambient atmosphere, a sensor film was formed and ready for use.

Example IX

Response and Recovery of the Water Sensor in Water-Containing and Water-Free Solvents FIGS. 8(a)–(e) show the phase angle decrease when the sensor was exposed to 20% $H_2O$ in (a) acetone, (b) acetonitrile, (c) methanol, (d) ethanol, and (e) 1,4-dioxane, and the phase angle increase when the sensor-containing flow-cell was refilled with corresponding $H_2O$-free solvents. The response and recovery occurred in seconds. In general, the phase angle changed range from 18° (methanol→20% $H_2O$ in methanol) to 36° (acetonitrile→20% $H_2O$ in acetonitrile). Such significant phase angle changes for water in alcohols enables the sensor to be used in monitoring beer production. Despite the relatively large noise, which may be reduced by selecting more data points, the data clearly show the usefulness of the sensor for measuring $H_2O$ in organic solvents.

Figure 9:
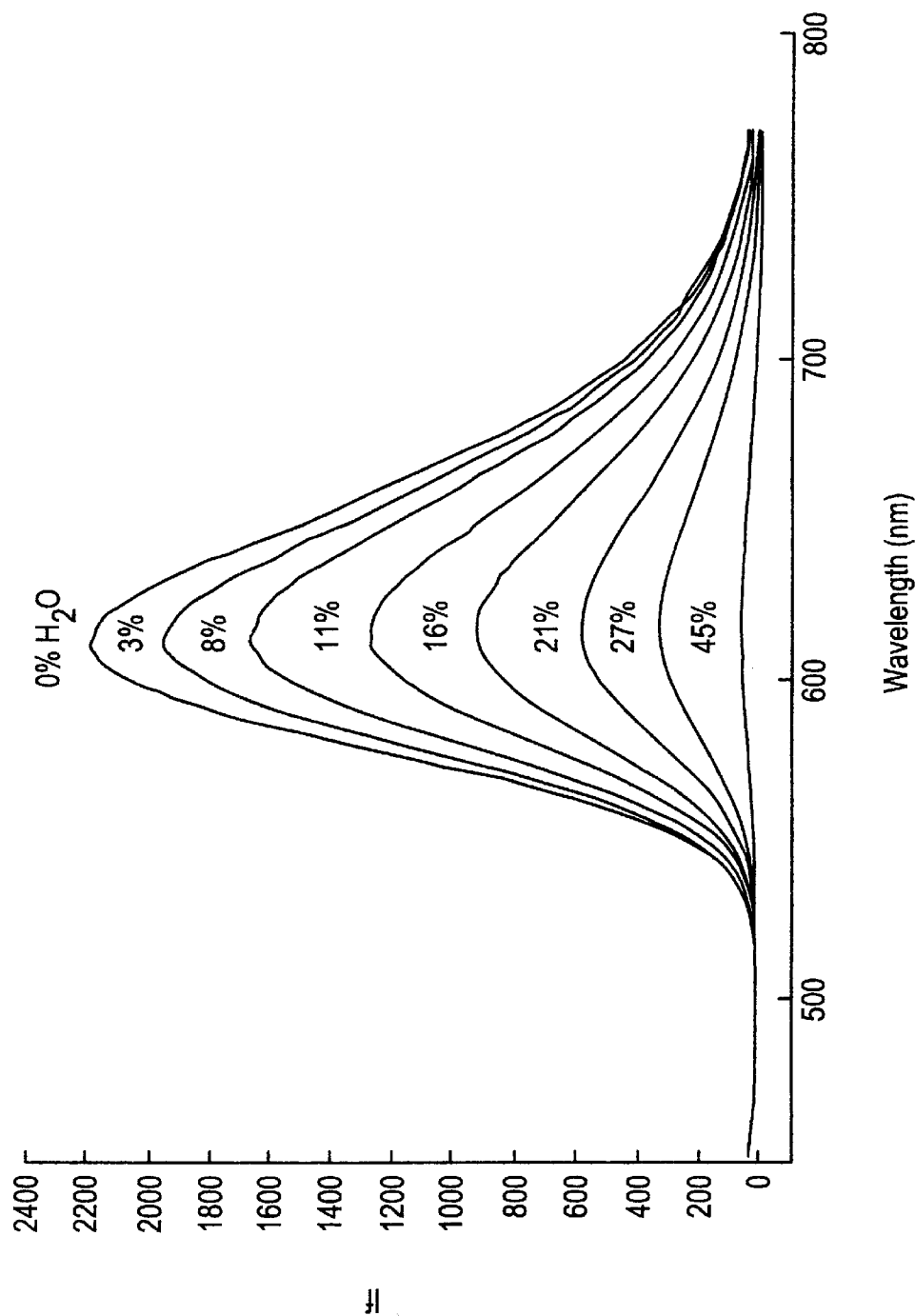
FIG. 9 shows the fluorescence emission spectra of $1.1 \times 10^{-5}$M $Os(dppz)$ $(dppe)_2(PF_6)_2$ in acetate with various concentrations of water.

FIG. 9 shows the fluorescence emission spectra of $1.1 \times 10^{-5}$M Os(dppz) $(dppe)_2(PF_6)_2$ in acetate with various concentrations of water. It is apparent from the figure that fluorescence intensity $(I_f)$ varies with the concentration of water.

The invention being thus described, it will be obvious to one of ordinary skill in the art that the same may be varied in many ways. Such variations are not to be regarded as a departure from the spirit and scope of the invention, and all such modifications are intended to be included within the scope of the following claims.

We claim:

1. A method for determining the presence, amount or concentration of a polar solvent, comprising the steps of:
   (i) providing a sensor having a transition metal-ligand complex comprised of a transition metal and at least one bi- or tri-dentate imine ligand;
   (ii) determining in the absence of the polar solvent, a luminescent lifetime characteristic of said transition metal-ligand complex;
   (iii) contacting said polar solvent with said sensor;
   (iv) determining a change in the luminescence lifetime of said sensor; and
   (v) determining the presence, amount or concentration of the polar solvent based on the change in the luminescence lifetime characteristic of said sensor.

2. The method according to claim 1, wherein said sensor comprises tris(4,4'-dicarboxy-2,2'-bipyridine)ruthenium (II) hexafluorophosphate.

3. The method according to claim 1, wherein said sensor comprises dipyridol[3,2-a:2",3"-c]phenazine, di[cis-1,2-bis(diphenylphosphino)-ethylene]osmium(II) hexafluorophosphate.

4. The method according to claim 1, wherein the polar solvent is selected from the group consisting of water, methanol, ethanol, propanol, butanol, ethylene glycol, and N-methylacetmide.

5. The method according to claim 1, wherein said luminescence lifetime characteristic is measured in frequency domain using phase-modulation fluorometry.

6. The method according to claim 5, further comprising:
   (a) irradiating said sensor with an amplitude modulated light, thereby causing said sensor to emit luminescence;
   (b) measuring the phase angle and/or phase modulation of the luminescence emitted by said sensor; and
   (c) calculating said luminescence lifetime from the measured phase angle and/or phase modulation.

7. The method according to claim 1, further providing:
   (a) an excitation light source for irradiating said light sensor; and
   (b) means for measuring a lifetime characteristic of luminescence emitted by said sensor.

8. The method according to claim 7, further providing means for eliminating scattered light and rendering the light from the excitation light source monochromatic.

9. The method according to claim 7, wherein the excitation light source is a light emitting diode (LED).

10. The method according to claim 7, further providing a optical transmission means for transmitting said luminescence excitation radiation to said sensor and a detector for receiving luminescence emitted by said sensor.

11. The method according to claim 10, wherein the optical transmission means is an optical fiber.

12. The method according to claim 1, further providing means for collecting, recording and graphically presenting luminescence lifetime characteristic and/or luminescence intensity measurements.

13. A method for determining the presence, amount or concentration of a polar solvent, comprising the steps of:
   (i) providing a sensor having a transition metal-ligand complex comprised of a transition metal and at least one bi- or tri-dentate imine ligand;
   (ii) determining in the absence of the polar solvent, the intensity of luminescence emitted by said transition metal-ligand complex;
   (iii) contacting said polar solvent with said sensor;
   (iv) determining a change in the luminescence intensity of said sensor; and
   (v) determining the presence, amount or concentration of the polar solvent based on the change in the luminescence intensity characteristic of said sensor.

14. The method according to claim 13, wherein said luminescence intensity is measured in time domain using pulsed or time-resolved fluorometry.

15. The method according to claim 13, wherein said sensor comprises tris(4,4'-dicarboxy-2,2'-bipyridine)ruthenium (II) hexafluorophosphate.

16. The method according to claim 13, wherein said sensor comprises dipyridol[3,2-a:2",3"-c]phenazine, di[cis-1,2-bis(diphenylphosphino)-ethylene]osmium(II) hexafluorophosphate.

17. The method according to claim 13, wherein the polar solvent is selected form the group consisting of water, methanol, ethanol, propanol, butanol, ethylene glycol, and N-methylacetamide.

18. The method according to claim 13, further providing:
   (i) an excitation light source for irradiating said light sensor; and
   (ii) means for measuring a lifetime characteristic of luminescence emitted by said sensor.

19. The method according to claim 18, further providing means for eliminating scattered light and rendering the light from the excitation light source monochromatic.

20. The method according to claim 18, wherein the excitation light source is a light emitting diode (LED).

21. The method according to claim 18, further providing a optical transmission means for transmitting said luminescence excitation radiation to said sensor and a detector for receiving luminescence excitation radiation emitted by said sensor.

22. The method according to claim 21, wherein the optical transmission means is an optical fiber.

23. The method according to claim 13, further providing means for collecting, recording and graphically presenting luminescence lifetime characteristic and/or luminescence intensity measurements.

* * * * *